United States Patent [19]

Stead

[11] Patent Number: 5,800,440

[45] Date of Patent: Sep. 1, 1998

[54] DEVICE FOR INSERTING A SURGICAL PIN

[75] Inventor: James R. Stead, Woonsocket, R.I.

[73] Assignee: Johnson & Johnson Professional, Inc., Raynham, Mass.

[21] Appl. No.: 819,259

[22] Filed: Mar. 18, 1997

[51] Int. Cl.$^6$ .................................................. A61B 17/56
[52] U.S. Cl. ............................................................ 606/104
[58] Field of Search ........................... 606/104, 72, 73, 606/61, 86, 87, 88, 96, 97, 98, 99, 100

[56] References Cited

U.S. PATENT DOCUMENTS

| | | |
|---|---|---|
| 964,922 | 7/1910 | Lewthwaite . |
| 1,521,265 | 6/1924 | Anderson . |
| 3,351,054 | 11/1967 | Florek . |
| 3,842,824 | 10/1974 | Neufeld . |
| 4,140,111 | 2/1979 | Morrill . |
| 4,549,538 | 10/1985 | Schadrack, III et al. . |
| 4,719,907 | 1/1988 | Banko et al. . |
| 4,773,407 | 9/1988 | Petersen . |
| 4,858,603 | 8/1989 | Clemow et al. . |
| 4,869,242 | 9/1989 | Galluzzo . |
| 4,901,712 | 2/1990 | Voegeli et al. . |
| 4,911,154 | 3/1990 | Vickers . |
| 4,978,350 | 12/1990 | Wagenknecht . |
| 5,098,383 | 3/1992 | Hemmy et al. . |
| 5,180,388 | 1/1993 | DiCarlo . |
| 5,398,861 | 3/1995 | Green . |
| 5,476,467 | 12/1995 | Benoist . |
| 5,486,178 | 1/1996 | Hodge . |
| 5,496,327 | 3/1996 | Den Ouden et al. . |
| 5,531,751 | 7/1996 | Schultheiss et al. . |
| 5,540,695 | 7/1996 | Levy . |

*Primary Examiner*—Guy V. Tucker
*Attorney, Agent, or Firm*—Nutter, McClennen & Fish, LLP

[57] ABSTRACT

An insertion device for a surgical pin includes a body defining a bore therein and a retainer disposed in the bore for frictionally engaging a portion of the surgical pin. The bore includes an aperture defining an entry into the bore, a surface for limiting the depth of insertion of the surgical pin, a wall surface extending from the insertion limiting surface, and a recess in the wall surface disposed between the aperture and the insertion limiting surface. In an exemplary embodiment, the retainer is an O-ring disposed within the recess. The O-ring defines a resilient aperture having a diameter less than that of the pin.

22 Claims, 4 Drawing Sheets

DEVICE FOR INSERTING A SURGICAL PIN

BACKGROUND OF THE INVENTION

Damaged and diseased joints which are no longer functional can be replaced by prosthetic joints, such as a knee joint during an arthroplasty. In order to prepare an area of a joint to receive a prosthetic joint component, angled cuts are made in a bone to resection it. The cuts must be accurate in order for the prosthetic joint components to be properly secured to the bone and for the joint to function without discomfort to the recipient and abnormal wear of the joint.

Various orthopaedic instruments, such as cutting guides, are often used to obtain accurate cuts in a bone. Typically, such a guide is secured to an end of a bone, such as a tibia, with surgical pins prior to resection. In many instances force must be applied to the surgical pins, typically with a surgical mallet, to insert the pins into bone. This task becomes complicated when a pin must be inserted at an awkward angle or where space constraints provide only limited access to the pin. Such complications increase the risk of inaccurate insertion of the pin and could compromise success of the surgery.

Another obstacle to effective pin insertion is that the pins, which are normally positioned and held in place during hammering, can become coated with bodily fluids and thus become quite slippery during a surgical procedure. This condition can cause pin handling and manipulation to become quite difficult. Furthermore, retractable pins associated with a cutting instrument, for example, may be difficult to access directly with a mallet. It will be appreciated that the above problems impart inefficiencies and extra time to a surgical procedure thereby increasing the risk to a patient.

SUMMARY OF THE INVENTION

The present invention provides a device useful to manipulate and insert surgical pins, such as Steinman pins. The pin insertion device has a mechanism for releasably retaining an end of the pin, and it also provides a means of imparting an accurate impact force to the pin.

The device for inserting a surgical pin includes a body portion having a first end defining a bore and a retainer disposed within the bore for releasably engaging a portion of the pin. The bore includes a surgical pin insertion limitation surface for limiting the depth to which the pin can be inserted into the device and a wall portion extending from the surgical pin insertion limitation surface to a first aperture which defines an entry into the bore. A recess within the wall portion is located at a point between the surgical pin insertion limitation surface and the first aperture. The retainer for releasably engaging a portion of the pin is at least partially disposed within the recess.

In one embodiment, the retainer is an elastically deformable O-ring which has an inner diameter less than a diameter of the pin. Upon insertion of the pin into the bore, portions of the O-ring in contact with the pin deform and frictionally engage the pin.

In a further feature of the invention, the body includes a second end defining an impact surface for receiving an impact. The force of the impact on the impact surface is transferred to a surgical pin engaged by the device at the pin insertion limitation surface. The impact surface enhances the ability of a surgeon to accurately apply a force to the surgical pin to insert the pin in a bone. An ergonomically contoured handle region can be provided intermediate the first and second ends of the device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
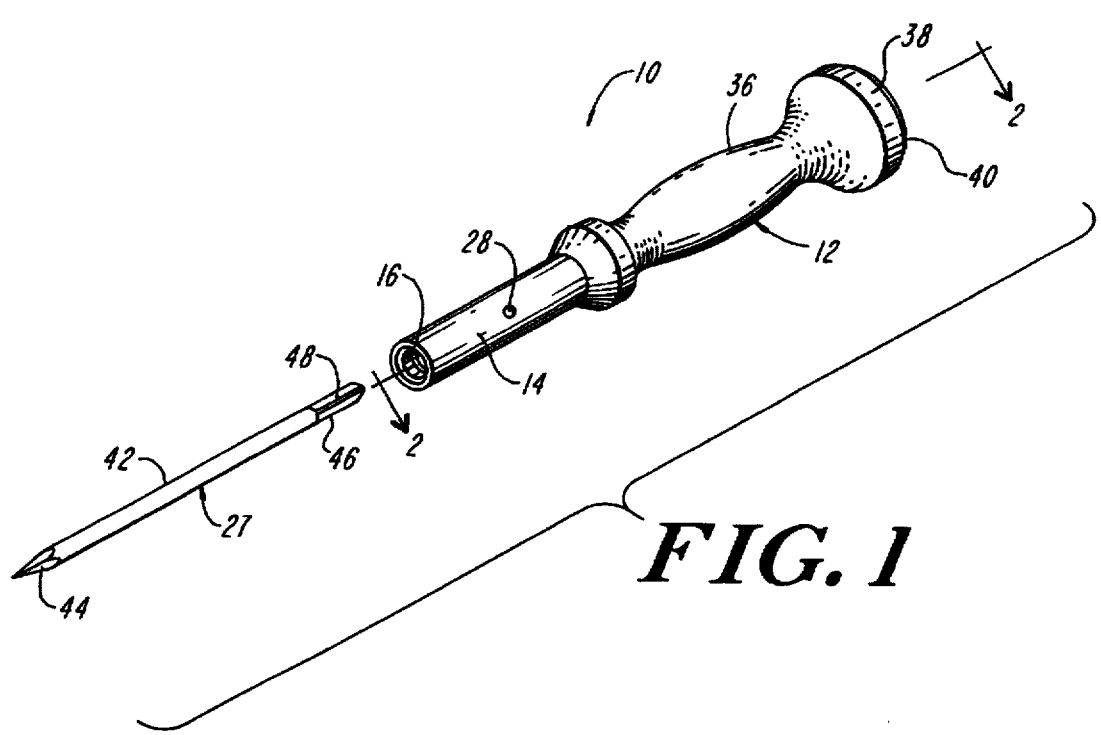
FIG. 1 is a perspective view of a surgical pin insertion device in accordance with the present invention.
Figure 2:
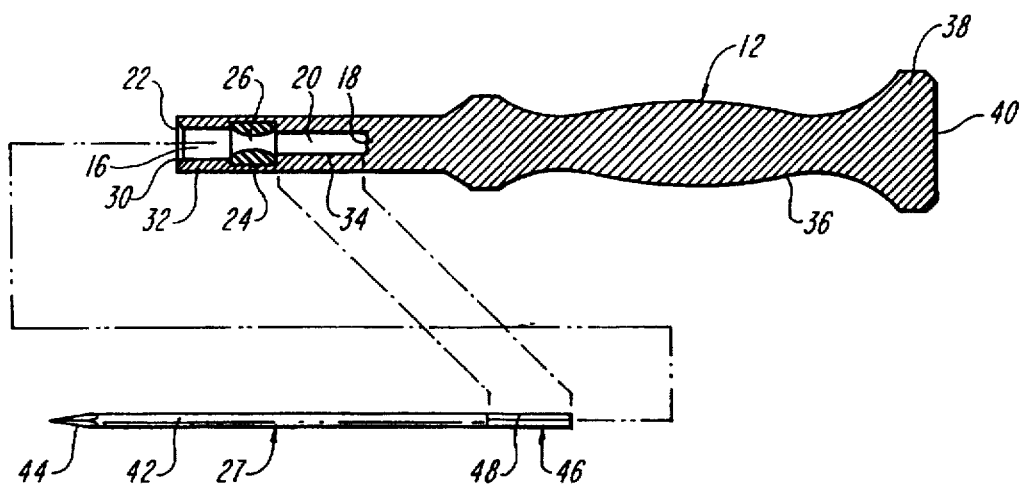
FIG. 2 is a cross sectional view of the surgical pin insertion device of FIG. 1.

Referring now to FIGS. 1 and 2, a surgical pin insertion device 10 includes a body portion 12 having a first end 14 defining a bore 16. The bore 16 includes a surgical pin insertion limitation surface 18 and a wall portion 20 extending from the surgical pin limitation surface to a first aperture 22 which defines an entry into the bore 16. A recess 24 within the wall portion 20 is located between the pin insertion limitation surface 18 and the first aperture 22. A retainer 26 is disposed within the recess 24 for releasably engaging a portion of a surgical pin 27.

Figure 3A:
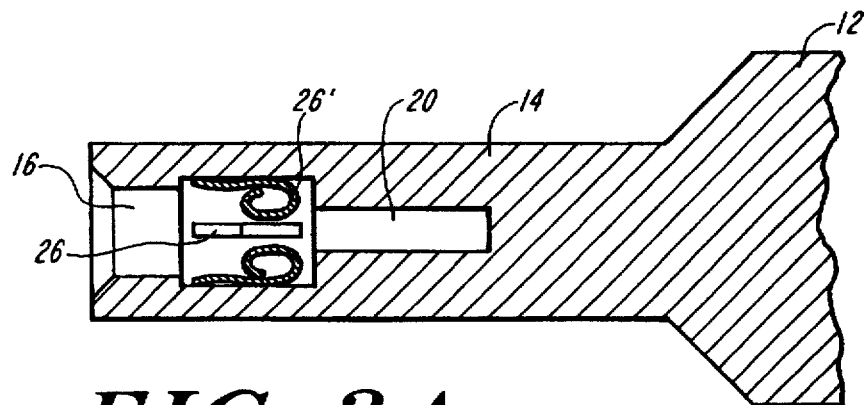
FIGS. 3A–3B are cross sectional views of alternative embodiments of the surgical insertion device of FIG. 1.
Figure 3B:
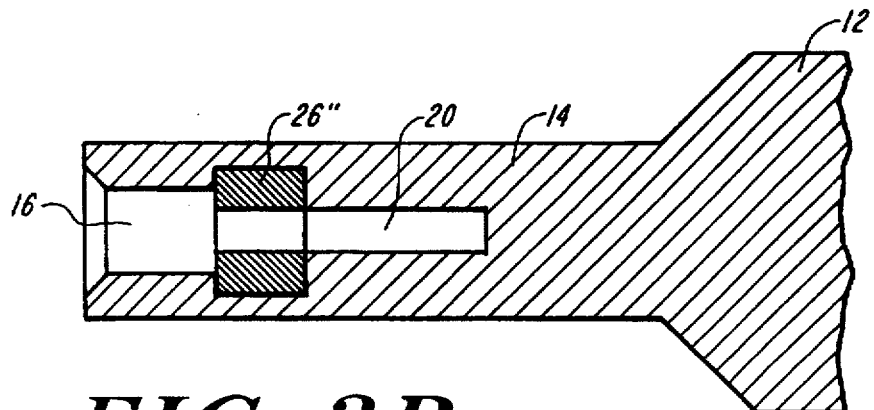

In the exemplary embodiment of FIG. 2, the retainer 26 is an elastically deformable O-ring disposed within the recess 24. The O-ring 26 defines an inner diameter less than a diameter of the surgical pin 27 at a portion of the pin insertable within the bore 16. The O-ring is formed from rubber in an illustrative embodiment, but other conventional elastomeric materials can also be used. In another embodiment shown in FIG. 3A, the retainer 26' comprises at least one biased retaining member or spring. In a further embodiment shown in FIG. 3B, the retainer 26" includes a magnetic element for engaging a pin.

The device 10 includes an optional second aperture 28 extending through the wall portion 20 into the bore 16 for providing a visual indication that the pin 27 is engaged in the bore. In other embodiments, the device includes further apertures having other shapes and sizes than that described herein.

In an exemplary embodiment, the device 10 has a frustoconical lip 30 which defines the first aperture 22 and guides an end of the pin 27 into the bore 16. A first section 32 of the wall portion adjacent the first aperture 22 defines a first diameter greater than a second diameter defined by a second section 34 of the wall portion. The larger diameter of the first section 32 enhances the ease of insertion of a pin 27 into the bore 16 while the smaller diameter of the second section 34 approximates a diameter of the pin 27 so that an elongate portion of the pin protruding from the bore rigidly extends from the device for precise positioning of the pin 27. As shown in the exemplary embodiment, the wall portion 20 of the bore 16 is smooth and cylindrical to accommodate a cylindrical surgical pin. In other embodiments, the wall portion is fluted or otherwise textured, while still maintaining the pin and bore in substantially concentric relation. Furthermore, the bore is not limited to a cylindrical shape, as other embodiments include a square or triangular bore.

In a further feature of the invention, the body 12 has a contoured external surface 36 for allowing a user to comfortably handle and precisely manipulate the device in a surgical environment. It will be appreciated by one skilled in the art that the dangerously sharp surgical pins often become wet and slippery during a surgical procedure and therefore are difficult to handle. Also, the pins are small as compared with the device and thus are less easily perceived by a user. The contoured body provides a way to efficiently and accurately position a pin. The contour of the device is not to be limited to that disclosed herein.

In an illustrative embodiment, the device 10 includes a second end 38 mushrooming into a flat, or slightly rounded, impact surface 40 for providing an increased surface area which can be struck with a surgical mallet, for example. The impact surface 40 is easily seen by a surgeon as compared with an end of a surgical pin. In addition, the significant surface area of the impact surface 40 reduces or eliminates occurrences of a surgeon missing the target and inadvertently striking an instrument or patient with the mallet.

An exemplary surgical pin 27 is a Steinman pin having a standard 0.125 inch diameter. The pin 27 includes an elongate portion 42 terminating in a sharpened insertion end 44 and a head portion 46. In an illustrative embodiment, the head portion 46 includes a plurality of beveled surfaces 48 which define a triangular cross section allowing the pin to be easily inserted into the bore 16.

Figure 4A:
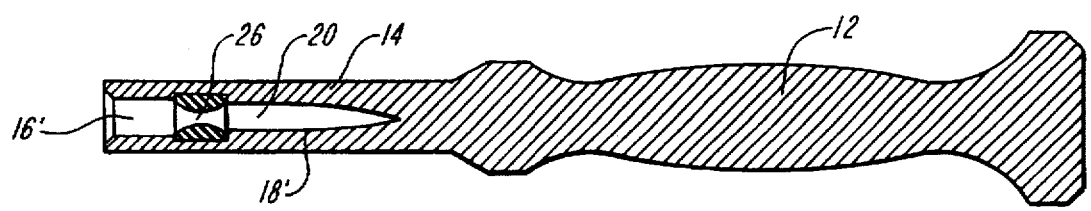
FIGS. 4A–4B are cross sectional views of further embodiments of the surgical pin insertion device of FIG. 1.
Figure 4B:
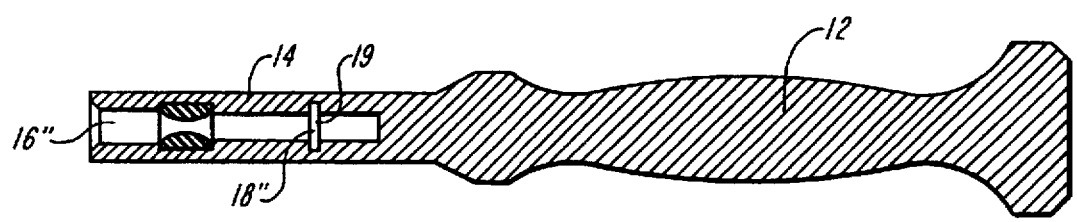

In the exemplary embodiment of FIG. 2, the pin insertion limitation surface 18 is a continuous surface terminating the bore 16. In another embodiment shown in FIG. 4A, a bore 16' progressively narrows to a point wherein a cross sectional area of the bore is less than that of the pin, thereby forming a pin insertion limitation surface 18'. In a further embodiment shown in FIG. 4B, a bore 16" continues beyond the pin insertion limitation surface 18" which is defined by a member 19 disposed across the bore. Other embodiments known to one of ordinary skill in the art to limit insertion of a pin are possible and within the scope of the present invention.

In operation, the head portion 46 of the pin 27 is inserted into the bore 16 until the head portion contacts the pin insertion limitation surface 18. The O-ring 26 is compressed at portions which contact the pin 27 thereby frictionally engaging the pin.

In an exemplary embodiment, upon reaching the maximum insertion depth, the O-ring 26 contacts a portion of the cylindrical, elongate portion 42 of the pin just beyond the triangular head portion 46 of the pin. This minimizes the force required to insert the pin 27 up to complete insertion and maximizes the force required to remove the pin by increasing the contact surface area, and therefore the friction, between the O-ring 26 and the pin at the point of complete insertion. Other embodiments of the device include differing bore depths and geometries adapted for pins of other shapes and sizes.

In an exemplary embodiment, a pin 27 engaged in the bore 16 is retained in any spatial orientation of the device and in the presence of movement of the device and significant inertial forces. The pin 27 is removed from the device with relative ease by applying a force aligned with a longitudinal axis of the pin, for example by pulling the device away from the pin after the pin has been inserted in a bone. It will be appreciated that the amount of force required to remove the pin from the device can be varied considerably depending upon the desired application. Selection of an O-ring inner diameter, coefficient of friction, and elasticity establish a predetermined disengagement force.

Figure 5:
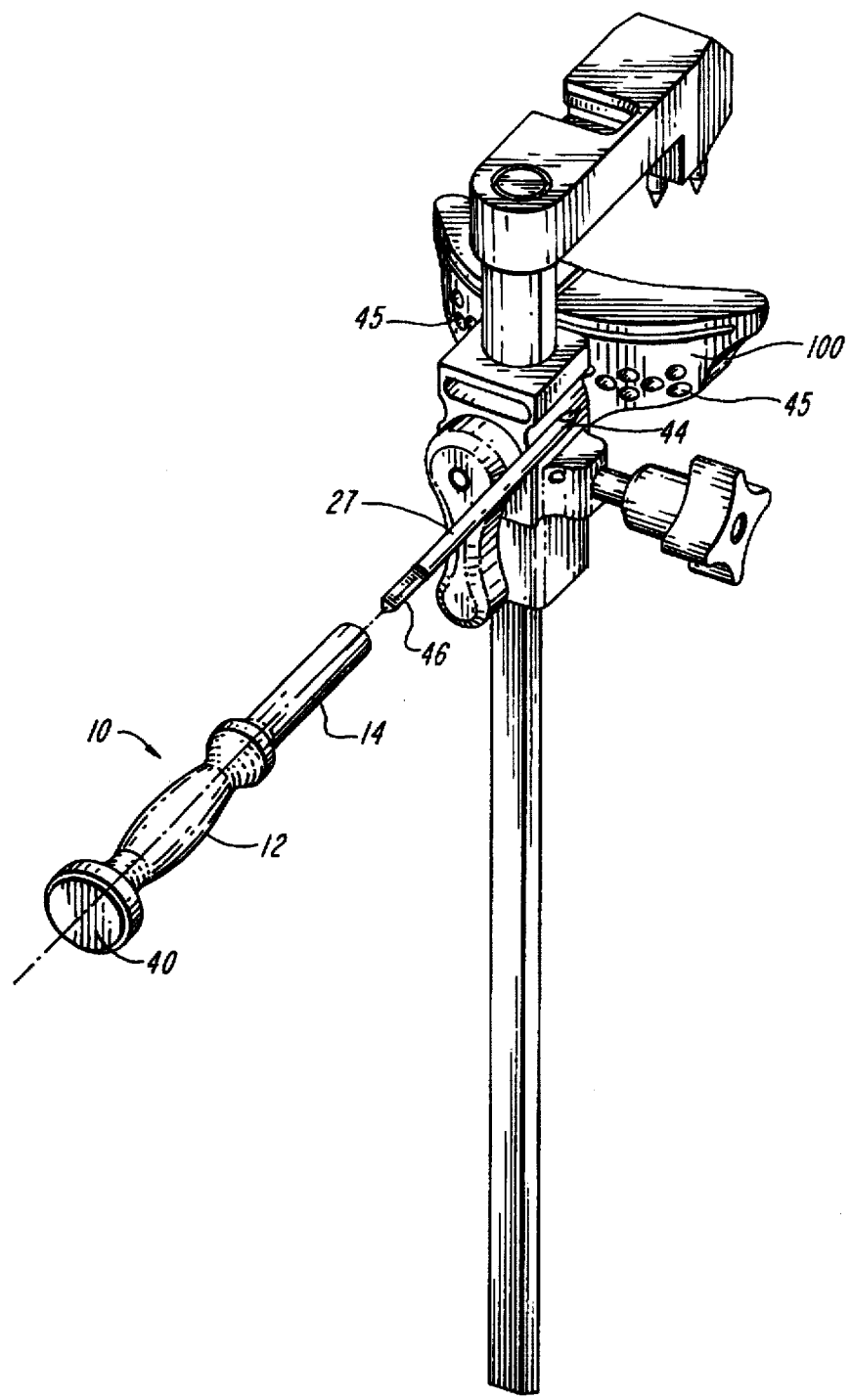
FIG. 5 is a perspective view of the surgical pin insertion device of FIG. 1 shown in conjunction with a conventional tibial cutting block orthopaedic instrument.

The surgical pin insertion device of the present invention is well suited for securing orthopaedic instruments to a bone of a patient. FIG. 5 shows the device 10 for inserting a surgical pin used in conjunction with a tibial cutting block 100. As will be appreciated by one of ordinary skill in the art, the cutting block 100 must be positioned and accurately secured to the bone in order to properly resect a tibia of a patient. To secure the cutting block 100, a series of surgical pins 27 are individually engaged by the device 10 and inserted into a bone through selected apertures 45 in the cutting block. The pin insertion device 10 releasably engages the head portion 46 of the surgical pin wherein the insertion end 44 of the pin is placed in a desired aperture 45. The impact surface 40 is hammered with a surgical mallet to insert the pin 27 to a desired depth. Thus, the device 10 provides a way for a surgeon to quickly and accurately secure the cutting block with the surgical pins.

Figure 6:
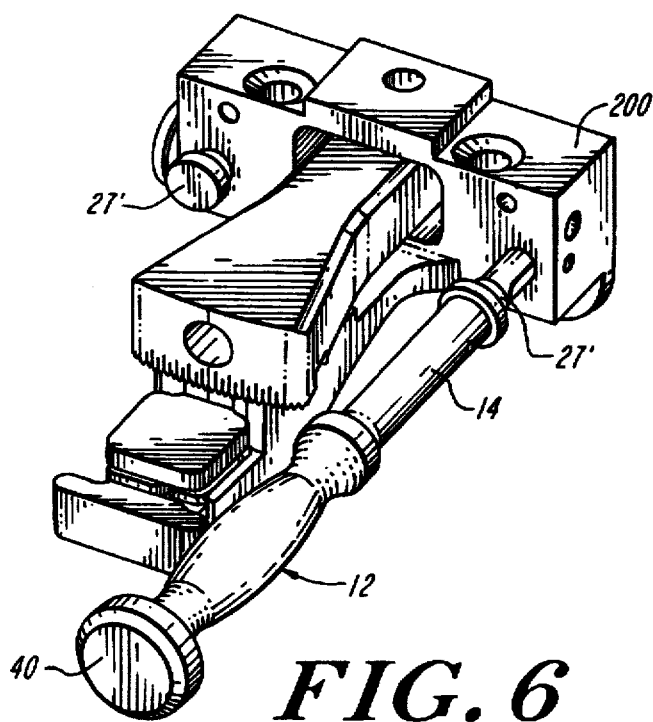
FIG. 6 is a perspective view of the surgical pin insertion device of FIG. 1 shown in conjunction with a conventional femoral locating orthopaedic instrument.

FIG. 6 shows the device 10 for inserting a surgical pin used in conjunction with a femoral locating device 200 which is secured with retractable pins 27'. Retractable pins 27' associated with an instrument are often difficult to access directly with a mallet or other impact means. The first end 14 of the device can be placed in contact with an end of the retractable pin 27' and the impact surface 40 of the device can be struck to insert the retractable pin into a bone of patient.

One skilled in that art will realize further features and advantages of the invention from the above-described embodiments. Accordingly, the invention is not to be limited by what has been particularly shown and described, except as indicated by the appended claims.

What is claimed is:

1. A device for inserting a surgical pin into solid bone, comprising:

a substantially linear, axially elongated body having a first end defining a bore effective to receive an end of the pin and a second end opposite the first end, the second end defining an outwardly facing impact surface for receiving a force to drive the pin into the solid bone, the bore including a surgical pin insertion limitation surface effective to transfer the impact force from the device to the pin, a wall portion extending from the surgical pin insertion limitation surface, and a first aperture defining an entry into the bore; and a retainer disposed within the bore effective to provide automatic releasable engagement of the pin in the bore, such that the device is removable from the pin while the pin remains secured in the solid bone.

2. The device according to claim 1, further comprising a recess within the wall portion located at a point between the surgical pin insertion limitation surface and the first aperture.

3. The device according to claim 2, wherein the retainer is at least partially disposed within the recess.

4. The device according to claim 3, wherein the retainer is an elastomeric member having an inner diameter less than that of the wall portion.

5. The device according to claim 1, further comprising a frusto-conical lip at the first end of the body portion.

6. The device according to claim 1, further comprising a second aperture extending through the wall portion into the bore.

7. The device according to claim 1, wherein the surgical pin insertion limitation surface transects the bore.

8. The device according to claim 1, wherein the wall portion progressively narrows to form the surgical pin limitation surface.

9. The device according to claim 1, wherein the surgical pin limitation surface comprises a portion of a member extending at least partially across the bore.

10. The device according to claim 1, wherein the retainer is an elastically deformable O-ring.

11. The device according to claim 1, wherein the retainer includes a magnetic element.

12. The device according to claim 1, wherein the retainer includes a biased retaining member.

13. The device according to claim 1, wherein the body portion is contoured to facilitate handling of the device.

14. The device according to claim 1, wherein the wall portion is smooth and cylindrical.

15. The device according to claim 14, wherein the impact surface defines a center point substantially aligned with a center point of the bore.

16. The device according to claim 1, wherein the wall portion includes a first portion and a second portion, the first portion being proximate the first aperture and defining a first cross sectional area of the bore greater than a second cross sectional area defined by the second portion.

17. A device for inserting a Steinman pin, comprising:

a handle portion including a pin receiving end and an impact end opposite the pin receiving end, the impact end defining an outwardly facing impact surface for receiving an impact force and the pin receiving end defining a bore having an inner surface terminating in an insertion limitation surface for transferring the impact force from the device to the pin, the inner surface including a first portion having a first diameter and extending from the insertion limitation surface and a second portion extending to an aperture defining an entry into the bore, and a channel circumscribed within the inner surface of the bore between the first and second portions of the inner surface; and an O-ring disposed at least partially in the channel for providing automatic releasable engagement of the pin in the bore.

18. A device for inserting a surgical pin into solid bone, comprising:

a body portion having a pin receiving end defining a bore and an outwardly facing impact end opposite the pin receiving end for receiving an impact force, the bore including a surgical pin insertion limitation surface for transferring the impact force to the pin, a wall portion extending from the surgical pin insertion limitation surface, a first aperture defining an entry into the bore, a frusto-conical lip defining the aperture, and a recess within the wall portion located at a point between the surgical pin insertion limitation surface and the first aperture, wherein the wall portion includes a first portion and a second portion having the recess therebetween, the first portion being proximate the first aperture and defining a first cross sectional area of the bore greater than a second cross sectional area defined by the second portion; and a retainer disposed within the recess for automatically releasably engaging an end of the pin inserted in the bore.

19. A device for inserting a surgical pin, the pin having an elongate portion and a head portion, wherein the device comprises:

a handle portion including a pin receiving end and an impact end opposite the pin receiving end for receiving an impact force thereon, the pin receiving end defining a bore having an inner surface including a first portion having a first diameter and terminating in an insertion limitation surface effective to transfer the impact force to the pin and a second portion extending to an aperture which defines an entry into the bore, and a recess disposed in the inner surface of the bore between the first and second portions of the inner surface; and an O-ring disposed at least partially in the recess;

wherein the head portion of the pin is insertable within the bore and frictionally engaged by the O-ring and the elongate portion of the pin rigidly protrudes from the device.

20. The device according to claim 19, wherein the head portion of the surgical pin includes at least one beveled surface.

21. The device according to claim 19, wherein the surgical pin is a Steinman type surgical pin.

22. The device according to claim 19, wherein the O-ring imparts a compressive force of a predetermined magnitude to the pin.

* * * * *